United States Patent [19]
Grandine

[11] 3,932,229
[45] Jan. 13, 1976

[54] METHOD OF SAMPLE APPLICATION TO GEL ELECTROPHORESIS MEDIA

[75] Inventor: Joseph D. Grandine, Acton, Mass.

[73] Assignee: Millipore Corporation, Bedford, Mass.

[22] Filed: Nov. 15, 1974

[21] Appl. No.: 524,040

[52] U.S. Cl............................. 204/180 G; 204/299
[51] Int. Cl.² ........................................ B01K 5/00
[58] Field of Search ............ 204/180 G, 180 S, 299; 23/253 R

[56] References Cited
UNITED STATES PATENTS

| | | | |
|---|---|---|---|
| 3,378,481 | 4/1968 | Saravis et al. | 204/299 |
| 3,482,943 | 12/1969 | Csizmas et al. | 204/299 X |
| 3,691,054 | 9/1972 | Cawley | 204/299 |
| 3,826,734 | 7/1974 | Godsey, Jr. | 204/299 |

OTHER PUBLICATIONS

Cawley, "Electrophoresis And Immunoelectrophoresis", (1969), Little, Brown and Co., Boston, Library of Congress No. 69–15086, pp. 230–235.

*Primary Examiner*—John H. Mack
*Assistant Examiner*—A. C. Prescott
*Attorney, Agent, or Firm*—Kenway & Jenney

[57] ABSTRACT

The invention concerns a method for the application of sample liquids to a gel type electrophoretic medium which leaves substantially no application artifact in the final electrophoretic pattern. The method consists of placing a cover sheet, having slits formed therein at the desired sample application locations, on the upper surface of the gel. An excess of sample is placed over each slit and allowed to remain in place for a fixed time period. It is then blotted to remove excess sample material and the cover is removed. Sample materials imbibed into the gel will then be appropriately located and in predetermined amounts depending on the gel porosity and time that the sample is in contact with the gel.

5 Claims, 3 Drawing Figures

METHOD OF SAMPLE APPLICATION TO GEL ELECTROPHORESIS MEDIA

BACKGROUND OF THE INVENTION

1. Field of the Invention

The invention relates to a method for the application of liquid samples to a gel type electrophoresis medium for subsequent separation by electrophoresis.

2. Description of the Prior Art

The use of porous gel media for electrophoresis has become significant in recent years, particularly slides or plates of agar and agarose gel. For example, procedures have been described using agarose gel which permit the separation of as many as 15 or 20 different protein-containing samples into their components simultaneously by electrophoresis in about an hour. While such procedures are known and are also useful, the application of samples to gel electrophoresis media has heretofore been a significant problem. The most common prior method was to form wells or slits in the gel surface either by forming them as the gel was formed or cutting the wells into the gel after formation. The liquid sample containing the materials to be separated by electrophoresis was placed in the well and electrophoresis was carried out in the normal fashion. This technique of forming the gel around a well-forming member as the gel is applied to the slide is described for example by B. G. Johansson in "Agarose Gel Electrophoresis", Scand. J. Clin. Lab. Invest. 29, Suppl. 114, Page 7 et seq, at page 10. One problem with this technique is that it leaves a "sample application artifact" in the completed electrophoretic pattern. If the stained pattern is scanned with automatic instrumentation to determine relative or absolute concentrations of the separated fractions, the results must be corrected to remove the effect of this sample application artifact. Further, the presence of the wells results in a discontinuity in the gel thickness with resulting higher current density in the gel below the well during electrophoresis. This higher current density in turn causes localized heating and drying of the gel media during electrophoresis.

Another problem with application of samples to wells cut in the gel media is that the wells had to be wide enough to accept a full drop. Such wells resulted in application areas which were not as narrow as might be desired.

To remedy this problem some workers in the field have attempted to place a mixture of gel and a predetermined amount of sample in the previously formed well. This is obviously a laborious and therefore expensive procedure.

Other application techniques that have been attempted include application of the sample to a carrier of paper, thread or cellulose strips and then applying the carrier with the sample thereon to the gel surface.

Another technique which has been used is the stab-application technique in which the sample is applied to the end of a pointed instrument, which is then inserted into the gel. As the instrument is removed the sample remains in the gel.

A further method which has been developed is the so-called "wire-pull" method in which the gel is formed in a frame with side walls. A wire supported by openings in the frame side walls is embedded in the gel. The sample is placed in contact with one end of the wire extending outside the frame. The wire is then pulled through the gel from the end opposite to that having the sample thereon and the sample is pulled into the gel as the wire passes through the gel.

From the foregoing it is apparent that no simple wholly satisfactory method of sample application to gels such as are used in electrophoresis has heretofore been developed.

SUMMARY OF THE INVENTION

The invention herein presented pertains to a novel method for the application of liquid samples to films of gel. It is particularly useful in the application of precise amounts of liquid sample to gel plates or slides used in electrophoretic separations of proteins. However it is also useful in other processes in which gel plates or slides are used, including immunoelectrophoresis and immunodiffusion. It is particularly adapted to the application of precise amounts of a number of different samples by relatively unskilled operators and has the advantage that it does not change the gel cross-section where applied, thereby obviating electrical discontinuities, and also does not leave a sample application artifact in the resulting electrophoresis pattern. Furthermore, the sample application is to a closely controlled area of the gel, which may have an advantageously narrow width.

Other features and objects of the present invention will become apparent from the following description and the accompanying drawing which forms a part of this application.

DETAILED DESCRIPTION OF THE PREFERRED EMBODIMENT

Figure 1:
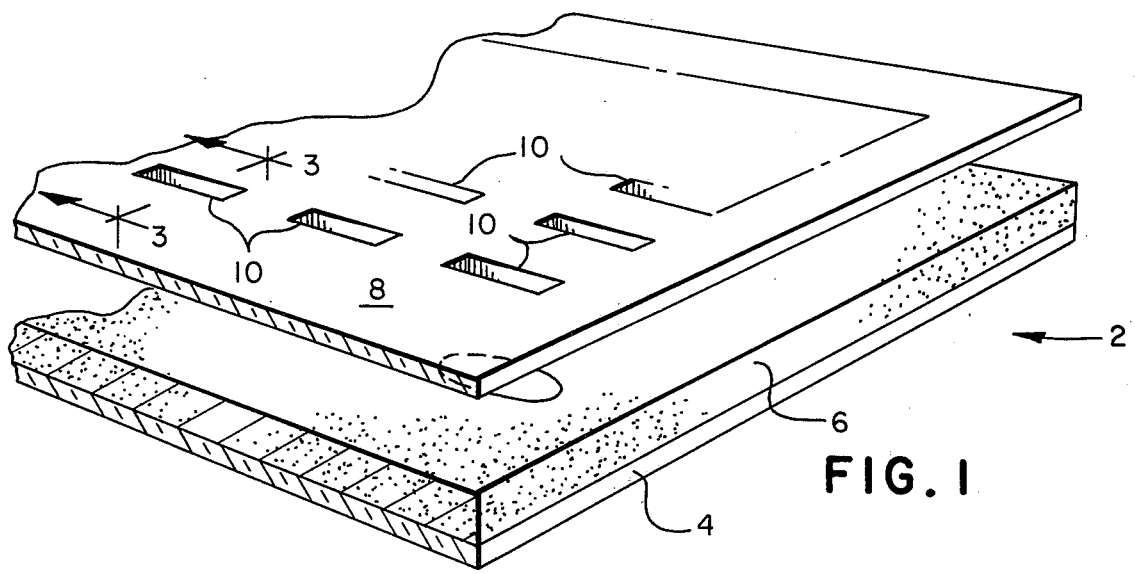
FIG. 1 is a perspective view, partially in section showing a slide of the type to which samples are to be applied with a sample application template located immediately above the slide.

FIG. 1, illustrates a slide, generally indicated at 2 having a base member 4 of glass or plastic and a gel layer 6 formed on the surface of the base member 4. A template 8 is shown positioned above the surface 6a of the gel layer 6 in the position it would occupy either just prior to being applied to the gel surface or just after being removed from the surface.

As shown in FIG. 1, a plurality of slits, 10 are formed in the template, these slits being the openings through which the sample is applied to the gel. Preferably the slits are formed along the same transverse line in the template with their narrow dimension paralleling the direction of electrophoretic migration in the gel and their long dimension at right angles to this direction.

The template 8 is preferably made of a plastic film material such as polyethylene. It is preferable that the plastic material itself not be wet by the sample so that when sample liquid is applied to its surface it remains as a globule or droplet on the surface and does not spread. Stated in another way, the contact angle between the sample and the material of the template should be greater than 90°.

Figure 2:
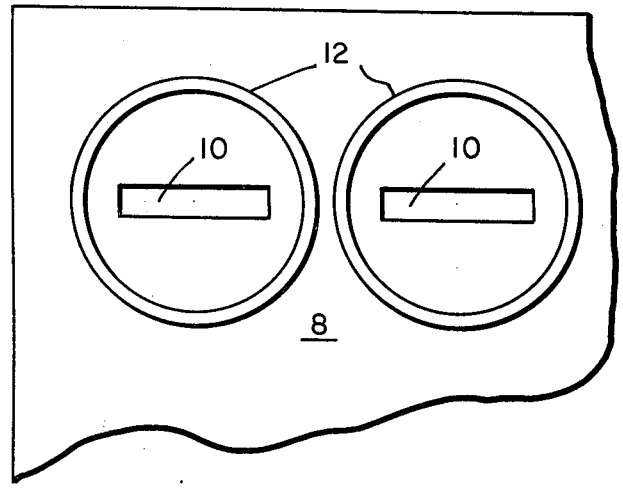
FIG. 2 is a top view of a template made of wettable material.

Alternatively, if the material of the template is wetted by the sample an upstanding ring 12, could be provided around each of the sample application slits as shown in FIG. 2 or a ring of non-wetting material such as silicone grease might be substituted for the actual upstanding rings 12 in FIG. 2.

In use, the template is laid over the upper surface of the gel with the slits 10 in the appropriate position into the gel.

Figure 3:
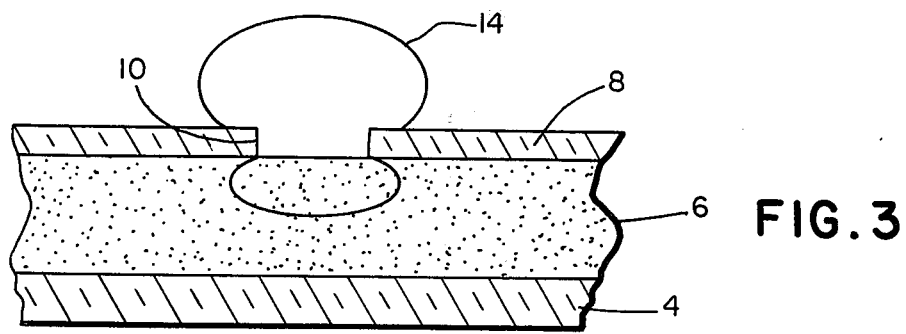
FIG. 3 is a section taken along the line of FIG. 1 showing the application template on the slide surface with an excess of sample on the template being imbibed into the gel.

A detailed cross-sectional view of the sample being imbibed into the gel is shown in FIG. 3. As there indicated, an excess of sample is placed on the template 8 covering the slit 10. This sample is imbibed by the porous gel 6, gradually diffusing into the gel. Using slits of a length of about 1 centimeter and a width of about 0.2 centimeters, we have found that an agarose gel having a concentration of 1.0% agarose at room temperature will absorb about 1 microliter of sample in approximately 100 seconds.

In practice, where samples from different sources are to be subjected simultaneously to electrophoretic action, the technician will apply the samples to the slits serially at predetermined times, for example every ten seconds. The technician starts a stop watch or other precise timing device as the first sample is applied and applies the sample serially in predetermined sequence at predetermined times, completing the applications before the total time that the sample is to be left in contact with the gel. Thereafter, the excess sample on the template is removed by blotting in the same sequence as the samples were applied. Alternatively the samples may be applied and removed simultaneously with a multiple pipetting device which would apply a drop of sample to each slit simultaneously. After an appropriate predetermined period the samples are blotted simultaneously to remove the excess sample. Either technique results in a predetermined volume of sample in the gel at a location determined by the slit in the template.

When the sample in the gel is subjected to electrophoretic action, and, as is usual, all the sample components are dissolved in the buffer solution which impregnates the porous gel, the application artifact will effectively disappear since under electrophoretic action all the components will be mobile, either as the result of electrophoresis or endosmosis.

It is important to note that once the sample or samples have been imbibed into the surface of the gel slide, the slide should be used for electrophoresis within a relatively short time such as for example within about 15 minutes, to minimize the effects of diffusion.

It will be seen from the foregoing that I have provided an improved sample application apparatus and procedure for applying samples to a gel slide for electrophoresis. By the use of my method and the apparatus described, precise amounts of the sample are imbibed into the gel slide at specified locations and, following electrophoresis, the sample application artifact disappears so that the location where the sample was applied is no longer apparent. The method avoids the laborious cutting or forming of wells into the gel surface with the attendant undesirable distortion of the electrostatic field across the gel during electrophoresis and is clearly superior to the prior sample application methods which have heretofore been practiced.

Having described my invention I claim:

1. The method of applying a sample liquid to a gel electrophoresis medium which comprises in combination the steps of:
   a. placing a cover sheet in contact with the surface of such gel medium, said sheet having a slit formed therein at the desired sample location;
   b. placing an amount of sample in excess of that to be absorbed by said medium over said slit,
   c. beginning measurement of a predetermined time when said excess sample is in place over said slit;
   d. blotting the unabsorbed sample from said slit at the end of the measurement of said predetermined time, whereby said excess sample is in place over said slit for a fixed and determined period; and
   e. removing said cover sheet from contact with the surface of said gel medium 2. The method defined in claim 1 in which said cover sheet is made of a material which is not wetted by said sample.

3. The method defined in claim 1 in which said cover sheet has a plurality of slits formed therein, whereby a plurality of samples may be applied to the surface of said gel.

4. The method defined in claim 3 which includes the steps of applying all of said samples simultaneously to said slits and simultaneously blotting said samples.

5. The method of applying sample liquids to a gel electrophoresis medium which comprises, in combination the steps of:
   a. placing a cover sheet in contact with the surface of said gel medium, said sheet having a plurality of slits formed therein at the desired sample application locations;
   b. sequentially placing an amount of sample in excess of that to be absorbed by said medium over each slit;
   c. beginning measurement of a predetermined time period for each slit when said excess sample is in place over said slit;
   d. blotting the unabsorbed sample from each slit at the end of the measurement of the predetermined time for said slit, whereby said excess sample is in place over said slit for a fixed and predetermined period; and
   e. removing the cover sheet from contact with the surface of said gel medium.

* * * * *